(12) United States Patent
Crow, Jr.

(10) Patent No.: US 10,105,407 B2
(45) Date of Patent: Oct. 23, 2018

(54) METHODS OF EXTRACTION OF NITROSYLATED OR NITRATED DERIVATIVES OF ASCORBIC ACID FROM MYRICIARIA DUBIA AND METHODS OF SYNTHESIS THEREOF

(71) Applicant: John P. Crow, Jr., Little Rock, AR (US)

(72) Inventor: John P. Crow, Jr., Little Rock, AR (US)

(*) Notice: Subject to any disclaimer, the term of this patent is extended or adjusted under 35 U.S.C. 154(b) by 0 days.

(21) Appl. No.: 15/177,987

(22) Filed: Jun. 9, 2016

(65) Prior Publication Data

US 2016/0361373 A1    Dec. 15, 2016

Related U.S. Application Data

(60) Provisional application No. 62/172,938, filed on Jun. 9, 2015.

(51) Int. Cl.
| | |
|---|---|
| *A61K 36/61* | (2006.01) |
| *C07D 307/32* | (2006.01) |
| *C07D 307/30* | (2006.01) |

(52) U.S. Cl.
CPC ........... *A61K 36/61* (2013.01); *C07D 307/30* (2013.01); *C07D 307/32* (2013.01); *A61K 2236/17* (2013.01); *A61K 2236/33* (2013.01); *A61K 2236/331* (2013.01); *A61K 2236/53* (2013.01)

(58) Field of Classification Search
CPC ...................................................... A61K 31/67
See application file for complete search history.

(56) References Cited

FOREIGN PATENT DOCUMENTS

GB    2114571 A  *  8/1983 ........... C07D 307/62

* cited by examiner

*Primary Examiner* — Benjamin J Packard
(74) *Attorney, Agent, or Firm* — Benjamin Aaron Adler

(57) ABSTRACT

The present invention relates to methods and strategies for extracting nitrosylated and/or nitrated derivatives and analogs from *Myriciaria dubia* fruit and for synthesizing the same. The ascorbic acid derivatives and analogs have the chemical structure of:

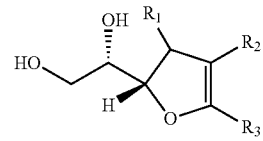

where $R_1$ is $=O$, $-ONO$, $-ONO_2$, or $-NH_2$; $R_2$ is $-OH$, $-ONO$, $-ONO_2$, or $-NH_2$; $R_3$ is $-OH$, $-ONO$, $-ONO_2$. The extraction method comprises freeze-drying the *Myriciaria dubia* fruit, mixing the freeze-dried powder with a solvent and separating and drying the supernatant. The synthetic method comprises derivatizing an ascorbic acid via nitrosylation and/or nitration in a buffered ascorbic acid solution, reducing zero or more nitro groups to an amine group, and purifying the ascorbic acid analog.

12 Claims, 11 Drawing Sheets

METHODS OF EXTRACTION OF NITROSYLATED OR NITRATED DERIVATIVES OF ASCORBIC ACID FROM MYRICIARIA DUBIA AND METHODS OF SYNTHESIS THEREOF

CROSS-REFERENCE TO RELATED APPLICATIONS

This non-provisional application claims benefit of priority under 35 U.S.C. § 119(e) of provisional application U.S. Ser. No. 62/172,938, filed Jun. 9, 2015, the entirety of which is hereby incorporated by reference.

BACKGROUND OF THE INVENTION

Field of the Invention

The present invention relates generally to the field of pharmaceutical chemistry. More specifically, the present invention is directed to methods of synthesizing ascorbic acid analogs and uses thereof.

Description of the Related Art

Pure nitric oxide (NO·) is often considered as a nitrosylating agent, which has been considered to possess a therapeutic effect on treatment of many ailments such as cardiovascular diseases, rheumatoid arthritis, cancer and Alzheimer's disease. Since the 1980s, extensive research have focused on nitric oxide (NO) donor drugs. A wide range of nitric oxide donors are being developed, each characterized by a particular pharmacokinetic and pharmacodynamic profile.

For instance, diazeniumdiolates (NONOates) have been discovered as nitric oxide donors in biological settings since the 1990s. Many studies have linked NONOates to therapeutic effects on cardiovascular and pulmonary disorders. S-nitrosothiol nitric oxide donors include a class of compounds which contain chemical bond between a thiol group and the nitric oxide moiety. Besides antithrombotic action that improves cardiovascular ailments, S-nitrosothiol compounds have neuroprotective properties. Many researchers have developed hybrid nitric oxide donor drugs, which are compounds derived by structurally modifying established drugs to incorporate nitric oxide molecules. These compounds have been purported to treat many disease or ailments including but not limited to cardiovascular conditions, inflammation or cancer.

Ascorbic acid is an essential vitamin for human health involving strong reducing ability to protect cells from damaging free radicals, especially harmful reactive oxygen species. Many studies have associated high dose ascorbic acid with cancer treatment.

Hence, it would be highly desirable to develop a compound that comprises ascorbic acid with potential nitric oxide release ability, which has enhanced therapeutic effects, relative to existing nitric oxide donor drugs. In addition to the antioxidant properties of ascorbic acid, such a compound also participates as a substrate/cofactor for some enzymatic processes. An analog of ascorbic acid might interfere with other biological (enzyme substrate) functions of ascorbic acid. Therefore, the ideal ascorbic analog with the property of antioxidant and nitric oxide donor should also be able to avoid interference with any enzymatic processes.

Thus, there is a recognized need for ascorbic acid analogs that are antioxidants and nitric oxide donors, but at the same time do not participate in an enzymatic process in a living organism as a substrate or cofactor. The prior art is deficient in these respects. The present invention fulfills this long standing need and desire in the art.

SUMMARY OF THE INVENTION

The present invention is directed to a method for synthesizing an $NO_{1-3}$ derivative of ascorbic acid. This method comprises the steps of derivatizing an ascorbic acid via nitrosylation and/or nitration in a buffered ascorbic acid solution to produce tge $NO_{1-3}$ ascorbic acid derivative.

The present invention is directed further to an ascorbic analog having a chemical structure of

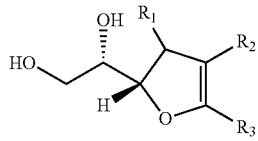

wherein $R_1$ is O, —ONO, —$ONO_2$, or —$NH_2$; $R_2$ is —OH, —ONO, —$ONO_2$, or —$NH_2$; $R_3$ is —OH, —ONO, —$ONO_2$.

The present invention is directed further to a method for synthesizing an ascorbic acid analog. The method comprises the steps of adding hydrogen peroxide to a stirred solution of ascorbic acid in sodium citrate buffer; adding sodium nitrite peroxide to the stirred solution of ascorbic acid in sodium citrate buffer; stirring the solution continuously for about 24 hours; reducing zero or more intro groups to an —$NH_2$ group; isolating and purifying the ascorbic acid analog.

The present invention is further directed to a method of preparing an extract from *Myriciaria dubia* fruit. First, the *Myriciaria dubia* fruit is freeze-dried. Then, the dry *Myriciaria dubia* fruit is added to a solvent. After agitating the mixture, it is stored at 4° C. The mixture is agitated again, and centrifugation is applied to obtain a supernatant. The extract of *Myriciaria dubia* fruit is finally obtained by drying the supernatant after centrifugation.

Other and further aspects, features, benefits, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

FIG. 2A shows the result of camu camu fruit water extract using mass spectrometry with HPLC Fx1. FIG. 2B shows the result of camu camu fruit water extract using mass spectrometry with HPLC Fx2.

FIG. 3A shows the HPLC result for camu water extract monitored at 340 nm. FIG. 3B shows the HPLC result for compound from synthetic reaction monitored at 340 nm.

FIG. 4A shows the optimized molecule structural geometry for authentic ascorbic acid obtained from ab initio molecular modeling. FIG. 4B shows the reactive electron density for or authentic ascorbic acid obtained from ab initio molecular modeling. FIG. 4C shows the optimized molecule structural geometry for 3-nitroso-ascrobic acid obtained from ab initio molecular modeling. FIG. 4D shows the reactive electron density for 3-nitroso-ascrobic acid obtained from ab initio molecular modeling. FIG. 4E shows the UV-visible spectra obtained from ab initio calculation for authentic ascorbic acid. FIG. 4F shows the actual measured UV-spectrum for authentic ascorbic acid. FIG. 4G shows the UV-visible spectra obtained from ab initio calculation for 3-nitroso-ascrobic acid. FIG. 4H shows the actual measured UV-spectrum for 3-nitroso-ascrobic acid.

FIG. 5A shows the optimized molecule structural geometry for putative 3-nitro-ascrobic acid obtained from ab initio molecular modeling. FIG. 5B shows the reactive electron density for or putative 3-nitro-ascrobic acid obtained from ab initio molecular modeling. FIG. 5C shows the optimized molecule structural geometry for 4-nitroso-ascorbic acid obtained from ab initio molecular modeling. FIG. 5D shows the reactive electron density for 4-nitroso-ascorbic acid obtained from ab initio molecular modeling. FIG. 5E shows the UV-visible spectra obtained from ab initio calculation for putative 3-nitro-ascrobic acid. FIG. 5F shows the actual measured UV-spectrum for putative 3-nitro-ascrobic acid. FIG. 5G shows the UV-visible spectra obtained from ab initio calculation for 4-nitroso-ascorbic acid. FIG. 5H shows the actual measured UV-spectrum for 4-nitroso-ascorbic acid.

DETAILED DESCRIPTION OF THE INVENTION

Figure 1:
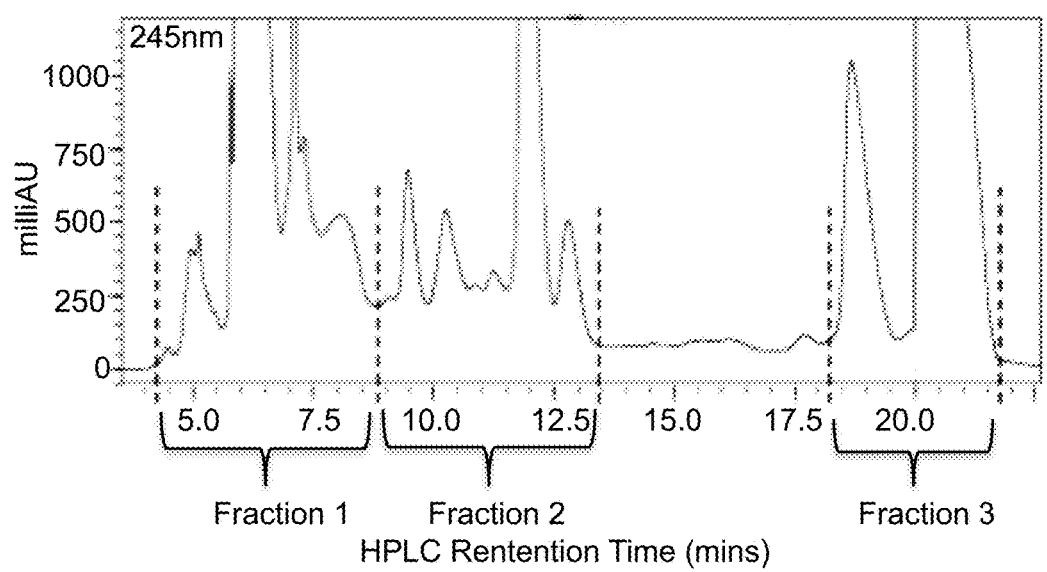
FIG. 1 shows the fraction collected for refined ultrafiltered aqueous camu camu fruit extract using High Performance Liquid Chromatography (HPLC).

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. The terms "comprise" and "comprising" are used in the inclusive, open sense, meaning that additional elements may be included.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "NOx" refers to a functional group comprising a nitrogen atom and a number of oxygen atoms. Generally, x is from about 1 to about 3.

In one embodiment of the present invention, there is provided a method for synthesizing a $NO_{1-3}$ derivative of ascorbic acid. This method comprises a step of derivatizing an ascorbic acid via nitrosylation and/or nitration in a buffered ascorbic acid solution to produce the $NO_{1-3}$ ascorbic acid derivative. In this embodiment, the derivatizing step comprises adding independently hyrogen peroxide and sodium nitrite peroxide to a stirred solution of ascorbic acid in a sodium citrate buffer to produce a peroxynitrite/peroxynitrous acid. Also, the molar rate for the hydrogen peroxide, the sodium nitrite, the ascorbic acid and the sodium citrate is 1:0.8:2:8. In addition, the peroxynitrite/peroxynitrous acid is at steady state in the solution.

Further to this embodiment, the method comprises reducing at least one nitro group to an —$NH_2$ group. In another further embodiment, the method comprises isolating and purifying the $NO_{1-3}$ ascorbic acid derivative. In all embodiments, the sodium citrate buffer may maintain the pH value of the solution at about 3.7. Also in all embodiments, derivatizing the ascorbic acid occurs over a period of about 24 hours.

In another embodiment of the present invention, there is provided a compound produced by the method described supra, having a chemical structure of:

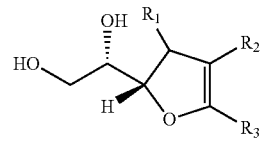

In this embodiment $R_1$ is =O, —OH, —ONO (nitrite), or —$ONO_2$ (nitrate) or —$NH_2$; $R_2$ is —OH, —ONO, —$ONO_2$ or —$NH_2$; $R_3$ is =O, —OH, —ONO, —$ONO_2$ or —$NH_2$. At least one of $R_1$, $R_2$ and $R_3$ contains nitrogen. Representative examples of the compound are 3-nitroso-ascorbic acid, 3-nitro-ascorbic acid, 4-nitroso-ascorbic acid, 4-nitro-ascorbic acid, 6-nitroso-ascorbic acid, or 6-nitro-ascorbic acid.

In yet another embodiment of the present invention, there is provided a pharmaceutical formulation, comprising the compound as described supra and a pharmaceutically acceptable delivery vehicle. Examples of the pharmaceutically acceptable delivery vehicle are a liposome, microspheres, nanoparticles, hydrogel, or a combination thereof.

In yet another embodiment of the present invention, there is provided a method for synthesizing an ascorbic acid analog. The method comprises the steps of adding hydrogen peroxide to a stirred buffered solution of ascorbic acid; adding sodium nitrite peroxide to the stirred solution of ascorbic acid; stirring the solution continuously for about 24 hours; reducing zero or more nitro groups to an amine group; isolating the ascorbic acid analog from the stirred solution; and purifying the ascorbic acid analog. In this embodiment, the stirred solution has a pH of about 3.7. In this embodiment, ascorbic acid analog has a chemical structure of:

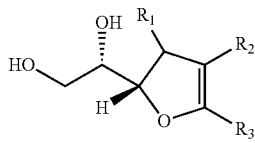

wherein $R_1$ is =O, —OH, —ONO, —ONO$_2$ or —NH$_2$, or —NH$_2$; $R_2$ is —OH, —ONO, —ONO$_2$, or —NH$_2$; $R_3$ is —OH, =O, —ONO, —ONO$_2$ or —NH$_2$, wherein at least one of $R_1$, $R_2$ and $R_3$ contains nitrogen. Preferably, the ascorbic analog is 3-nitrosos-ascorbic acid, 3-nitro-ascorbic acid, or 4-nitroso-ascorbic acid.

In another embodiment of the present invention, there is provided a method of preparing an extract from *Myriciaria dubia* fruit comprising the steps of freeze-drying *Myriciaria dubia* fruit; adding solvent to freeze-dried *Myriciaria dubia* fruit; agitating a mixture of freeze-dried *Myriciaria dubia* fruit and the solvent; storing the mixture at about 4° C.; agitating the mixture; centrifuging the mixture to obtain a supernatant; and drying the supernatant to obtain an extract of *Myriciaria dubia* fruit.

Further to this embodiment, the method may comprise a step of ultrafiltering the supernatant with a molecular weight cut-off centrifugal filter apparatus. In this further embodiment, a cut-off molecular weight for the centrifugal filter apparatus is about 3 kD or about 5 kD. In another further embodiment, the method may comprise a step of refining the extract using high performance liquid chromatography. In all embodiments, the solvent may comprise water, ethanol or a combination thereof. Also in all embodiments, the weight of *Myriciaria dubia* fruit to volume of the solvent volume is about 1:10.

Provided herein are ascorbic acid analogs that are nitric oxide donor compounds while retaining the property of antioxidants. These analogs comprise 3-nitroso-ascorbic acid, 3-nitro-ascorbic acid, and 4-nitroso-ascorbic acid. These compounds are most unlikely to be substrates for any enzymatic processes involving the ascorbic acid, and therefore are useful as "pure" antioxidants that do not interfere with other biological functions of ascorbic acid.

Provided herein are methods and strategies for synthesis of ascorbic acid derivative and analog compounds and pharmaceutical compositions thereof and the compounds synthesized by the methods. For example, the compounds may comprise an NO$_x$ group, for example where x is 1, 2 or 3, such as 3-nitrosos-ascorbic acid, 3-nitro-ascorbic acid, and 4-nitroso-ascorbic acid. Also provided are methods of extracting the ascorbic acid derivative and analog compounds from *Myriciaria dubia* (camu camu). The pharmaceutical compositions may comprise one or more compounds or extracts and a pharmaceutically acceptable delivery vehicle such as are known and standard in the art. For example, but not limited to, representative delivery vehicles may be liposomes, microspheres, nanoparticles, hydrogels, or a combination thereof.

Synthesis of ascorbic acid derivatives/analogs is accomplished by nitrosylating and/or nitrating ascorbic acid using peroxynitrite/peroxynitrous acid. The peroxynitrite/peroxynitrous acid is produced by rapidly mixing sodium nitrite with a hydrogen peroxide/hydrochloric acid mixture, followed by immediate (within a few milliseconds) quenching with sodium hydroxide to make sodium peroxynitrite, which is much more stable than peroxynitrous acid. At low pH, ONOO⁻/ONOOH is formed when sodium nitrite is protonated to form nitrous acid (HNO$_2$), which decomposes to form nitrosonium ion (NO⁺) and attacks hydrogen peroxide.

The synthesized ascorbic acid derivatives and analogs and the *Myriciaria dubia* (camu camu) extracts exhibit antioxidant properties or are nitric oxide donors, but not a substrate or cofactor for an enzymatic process in a living organism. Thus, these compounds may be used as therapeutics to treat pathophysiological conditions requiring such effects. As is known in the art, the skilled person is well-able to determine dose, dosage regimens and routes of administration depending on the condition to be treated and the subject requiring treatment.

As described below, the invention provides a number of advantages and uses, however such advantages and uses are not limited by such description.

Example 1

Method for Extracting and Purifying NO$_x$AA from *Myriciaria dubia* Aqueous Extract Freeze-dried *Myriciaria dubia* fruit powder was extracted in nine volumes of water (2 grams powder to 18 ml water) to produce a 1:10 aqueous extract (AE). Water was added to pre-weighed powder, followed by vigorous mixing, and storage at 4° C. After 48 hours at 4° C., the aqueous extract was vigorously mixed again, and then subjected to centrifugation at 2,500×g for 10 minutes. Aqueous extract supernatant was decanted to a clean vial, and an aliquot (roughly ⅓$^{rd}$ of total volume) was taken to dryness using a centrifugal vacuum evaporation device (room temperature, overnight). This dried, non-ultrafiltered aqueous extract supernatant represents the sum of total water-soluble compounds in *Myriciaria dubia* fruit powder. Therefore, it is the "gold standard" by which all other extracts will be compared. From this point on, it is referred to as "AEstd", for Aqueous Extract Standard.

Ethanolic Extract

*Myriciaria dubia* fruit powder was extracted with 100% ethanol (nine volumes) just as described above for aqueous extraction to give a 1:10 ethanolic extract (EE). Ethanolic extract was then subjected to 5 kD ultrafiltration using a centrifugal ultrafilter apparatus. However, unlike aqueous extract, where a reddish-brown residue remained on the ultrafilter membrane, no residue was seen when ethanolic extract was ultrafiltered. Moreover, no change in color or appearance of ethanolic extract was noted after ultrafiltration. Thus, from that point on, ethanolic extract was prepared solely by 2,500×g centrifugation of powder/ethanol mix, without subsequent ultrafiltration. Non-ultrafiltered ethanolic extract was taken to dryness as described previously in the aqueous extract section.

Aqueous/Ethanol Extract

*Myriciaria dubia* (camu camu) fruit powder was extracted with a 1:1 mix of water and ethanol (nine volumes total) just as described above for aqueous extraction to give a 1:10 aqueous/ethanolic extract (AEE). Aqueous/ethanolic extract was also subjected to 5 kD ultrafiltration and ultrafiltrate collected and taken to dryness as described above.

Refining *Myriciaria dubia* Extract

The 3 kD ultrafiltered aqueous extract (AE-UF3) was subjected to High Performance Liquid Chromatography (HPLC) fractionation using a semi-preparative 10×250 mm Waters™ ODS-2 reversed phased column, eluted with 50 mM formic acid plus methanol (98:2% isocratic, then 10:90% from 13 to 20 minutes). Fractions were collected as shown in the FIG. 1.

Fraction 1 (most hydrophilic) consists of all compounds eluting from 4.3 to 8.8 minutes. Fraction 2 (intermediate hydrophobicity) consists of all compounds eluting from 8.8 to 13 minutes. Fraction 3 (most hydrophobic) consists of all compounds eluting from 18.2 to 21.7 minutes. All three HPLC fractions were collected in bulk, and dried as described above.

Description of Extracts

Analytical HPLC analysis reveals the following order of complexity in terms of the total number of abundant peaks at 254 nm (not shown): aqueous>aqueous/ethanolic> ethanolic. This indicates that more of the total chemical/biological properties of camu fruit powder are likely contained in the aqueous extract, and justifies it as the standard of comparison, and as the starting material for further fractionation using HPLC. However, prior to HPLC fractionation, aqueous extract is ultrafiltered with a 3,000 molecular weight cut-off filter to remove any large moelcules (polysaccharides, large glycoproteins, etc.), which would be highly retained on the HPLC column, leaching off over time and contaminant future fractions. Comparison of ultrafiltered aqueous to non-ultrafiltered aqueous ultimately determines whether desirable activities exist in the higher molecular weight fractions. That is, the absence of any biological activity in ultrafiltered extract filtrates (relative to AEstd) would indicate that chemical entities in the retentates (higher mass) are significant, whereupon retentates would be dried down and tested as new extracts.

Fractionation using reversed-phase HPLC yields extracts that are broadly based on relative hydrophilicity/hydrophobicity. The resolving power of a semi-preparative HPLC column is limited, thus the chemical complexity of the three extracts cannot reliably be assessed by a chromatogram alone. The compounds present in highest abundance mask minor co-eluting, or closely eluting peaks, which likely number in the dozens, and possibly in the hundreds. Thus, while HPLC fractionation yields extracts containing compounds of similar hydrophilic/hydrophobic properties, these extracts are still relatively complex in overall composition. While the fractionation process does not alter chemical composition per se, compounds which were minor components in the simple aqueous fruit powder extract (AEstd) can become more concentrated, and the relative amounts of different compounds can be dramatically altered. That is, none of the extracts contain anything that was not in the for aqueous extract standard (or in camu camu fruit powder), but compounds that represented 1% of the soluble mass in the aqueous extract standard, may be 5%, or 10% of the soluble mass in more refined extracts. In this way, the more refined extracts should be more potent, on a milligram per milligram basis, than aqueous extract standard—one of the intended goals of extract production. However, it should be emphasized that no extract can contain chemical entities that do not exist in *Myriciaria dubia* (camu camu) fruit powder.

Example 2

Testing of Extracts for Chemical and Biological Properties

The chemical and biological properties of five types of extracts from the *Myriciaria dubia* including aqueous extract without ultrafiltration (AEstd-nonUF), ethanolic extract without ultrafiltration (EE-nonUF), aqueous/ethoanolic extract without ultrafiltration (AEE-nonUF), aqueous extract with 5 kD ultrafiltration (AE-UF5) and queous.ethanolic extract with 5 kD ultrafiltration are tested. Three HPLC fractions including a most hydrophilic fraction (HPLC1), an intermediate hydrophobic fraction and a most hydrophobic fraction are investigated.

Chemical Properties

A basic comparison is done using the standard measurement of overall antioxidant capacity (ORAC). This allows direct comparison of extracts relative to the *Myriciaria dubia* fruit powder, represented by the non-ultrafiltered aqueous extract (AEstd). The antioxidant capacity for each extract relative to simple fruit powder extract is analyzed. The molecular weight of each compound in relation to antioxidant capacity is also determined. The overall antioxidant capacity test also provides the basis for quality control and chemical stability. Other assays related to redox activity, scavenging of radical and oxidative species, and nitric oxide releasing activity will be assessed in simple buffer solution, and in complex biological milieu.

Biological Properties

Cell-based assays are used for analyzing biological properties such as standardized anti-inflammatory, immune boosting, neuroprotective, smooth muscle relaxation, estrogen mimetic activity (anti-menopausal), antiviral, antibacterial, antifungal, antidepressant, appetite suppression. The nitroso- and/or nitro-containing compounds described above may be nitric oxide donors under biological conditions, consistent with reports of vasodilatory effects. While multi-component extracts are being tested and compared to camu fruit powder extract (AEstd), the nitroso- and nitro-containing compounds are purified and tested individually for nitric oxide-related properties (vasodilation, cell signaling, etc.), as well as broader biological properties, using a variety of cellular endpoints. Significant activities associated with these pure compounds would provide the basis for preparation and testing of chemical analogs. Neither nitroso-ascorbate nor nitro-ascorbate has ever been reported in chemical synthetic or biological literature. They have the potential to be prototypes for entirely new drug classes with unique biological properties.

Historical uses include the treatment of menopausal symptoms, which may be related to estrogen mimetic activity. Biologically-relevant activity in any in vitro or cell-based assay initially be assessed using the simple fruit powder aqueous extract (AEstd). Positive results with this extract, which contains all water-soluble compounds present in *Myriciaria dubia* (camu camu), provides the framework to compare extracts containing chemical sub-sets of *Myriciaria dubia* fruit. Sub-set extracts may lack the wide array of activities of the fruit extract, or may possess some activities of aqueous extract standard and not others. Using this process of comparative testing, the ultimate goal of assigning specific beneficial biological properties to chemical entities in *Myriciaria dubia* (camu camu) can be achieved. In the interim, the extracts should provide more potent versions of aqueous extract standard, perhaps possessing select biological properties which make them better suited for specific health benefits. That is, aqueous extract standard may possess five or six beneficial properties, while another extract possesses only one but more potent property, on a milligram per milligram basis.

Those biological properties that prove most significant in cell-based assays are explored further in animal models. For example, the ovarectomized mouse or rat provides an ideal model to examine compounds useful for treating menopausal symptoms. While estrogen mimetic activity could be assessed in cells, non-estrogen-dependent mechanisms for easing menopausal symptoms (hot flashes, low libido, etc.) can only be examined in whole animals, where broader physiological effects can be monitored. Other potential health benefits such as appetite suppression and cognitive enhancement can only be properly assessed in whole animals. Any potential "crossover" from health-related benefits of *Myriciaria dubia* (camu camu) to medical indications are rigorously examined in whole animal models and actively pursued in a more formal manner, i.e., formal drug development as opposed to neutraceutical/nutritional supplement. A medical indication, particularly for a single compound purified from *Myriciaria dubia* (camu camu) requires a fundamentally different approach, e.g., ADME (absorption, distribution, metabolism, and excretion) studies, animal efficacy studies, and ultimately an investigational new drug application to the Food and Drug Administration.

Based on historical uses for *Myriciaria dubia* (camu camu) in Amazonian cultures, and in North America, several health benefits can be validated in cell and animals. One or more extracts are expected be qualitatively and/or quantitatively better than *Myriciaria dubia* (camu camu) fruit powder, and therefore marketable as a nutritional supplement, either as a standalone product, or an additive to other supplements.

Example 3

Method for Synthesizing $NO_xAA$

Hydrogen peroxide (12.5 mM) and then sodium nitrite (10 mM) were added to a stirred solution of 25 mM ascorbic acid (AA) in 100 mM sodium citrate buffer at pH 3.7. Then, the reaction mixture was kept at room temperature for 24 hours, whereupon the solution revealed a deepening yellow color, consistent with nitro-containing compounds. HPLC analysis of this reaction mixture revealed two peaks that were slightly more retained than ascorbic acid itself, and which possessed the absorbance (320 to 400 nm) characteristic of nitrated ring structures. This solution was stored at about 4° C. overnight, and examined again on two subsequent days. The HPLC analysis revealed that the solution composition was unchanged, indicating that the reaction had gone to completion and that the putative NOx-ascorbic acid species were relatively stable.

This method is based on producing peroxynitrite/peroxynitrous acid ($ONOO^-/ONOOH$) in situ over the course of several hours. The standard method for making $ONOO^-/ONOOH$ is to rapidly mix sodium nitrite with a hydrogen peroxide/hydrochloric acid mixture, followed by immediate (within a few milliseconds) quenching with sodium hydroxide to make sodium peroxyntrite, which is much more stable than peroxynitrous acid. At low pH, $ONOO^-/ONOOH$ is formed when sodium nitrite is protonated to form nitrous acid ($HNO_2$), which decomposes to form nitrosonium ion ($NO^+$) and attacks hydrogen peroxide.

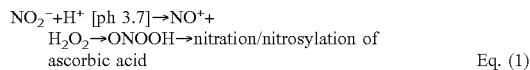

$$NO_2^- + H^+ \text{ [ph 3.7]} \rightarrow NO^+ + H_2O_2 \rightarrow ONOOH \rightarrow \text{nitration/nitrosylation of ascorbic acid} \quad \text{Eq. (1)}$$

Under the conditions used to make $NO_xAA$ (pH 3.7 versus ~pH 1), peroxynitrous acid is formed more slowly, but then decomposes more slowly, generating a steady-state concentration of $ONOO^-/ONOOH$, which is apparently critical to nitrating (addition of $-NO_2$ group) and/or nitrosylating (addition of $-NO$ group) ascorbic acid. Indeed, bolus addition of pre-synthesized peroxynitrite to ascorbic acid solutions failed to produce any stable $NO_xAA$ species. Production of $ONOO^+/ONOOH$ was confirmed in a separate reaction involving the same reactants but using 4-hydroxphenylacetic acid (5 mM) as the target molecule. Hydroxyphenylacetic acid is well-known to be readily nitrated by $ONOO^+/ONOOH$, and production of 3-nitro-4-hydroxyphenylacetic acid was confirmed by HPLC.

Two main products from the synthetic reaction match two dominant compounds in the camu water extract in terms of retention time on HPLC and UV-visible spectra (peaks #1 and 2, FIGS. 3A-3B); a third peak from camu extract and the synthetic reaction has a similar spectra and may be a geometric isomer (FIGS. 4E-4H). The simplicity of the synthetic reaction greatly limits the possible products to nitroso- and nitro-containing compounds, and oxidized (ring-opened) products of ascorbic acid. This fact, in turn, helps in putative identification of the novel compounds from camu camu.

Example 4

Reaction Mechanisms
Significance of the Reaction Mechanisms

The reaction mechanism, conditions, and dynamics (to generate $NO_xAA$) for synthesis of $NO_xAA$ are important because they may explain how/why the camu plant synthesizes copious quantities of $NO_xAA$. Camu camu (*Myriciaria dubia*) thrives in the acidic waters (pH 2.7) of the Amazon River; such growing conditions could promote nitration/nitrosylation of ascorbic acid and other compounds in camu via a chemical, non-enzymatic mechanism. A non-enzymatic reaction mechanism would suggest that camu produces a number of nitrated/nitrosylated compounds, as there is little or no specificity (relative to an enzyme-driven process).

Examination of Another Possible Reaction Mechanisms

In terms of alternative reaction mechanisms, the most common nitrosylating (adding an NO group) mechanism is via nitrous acid ($HNO_2$). Nitrous acid is readily formed when inorganic nitrite ($NO_2^-$) is acidified (pKa ~3.1). Nitrous acid spontaneously decomposes to $NO^+$ (nitrosonium ion) and $OH^-$ (hydroxide anion). Nitrosonium ion is highly oxidizing and capable of adding an $-NO$ group to many molecules with nucleophilic (electron-rich) groups, such as $-SH$, to give a nitrosothiol, or to amines ($-NH$) to give toxic nitrosamines, as happens when nitrite food preservatives are ingested and enter the pH 1-2 environment of the stomach. Ascorbic acid has long been known to inhibit nitrosamine formation, thus it must react with nitrosonium ion. However, no stable nitrogen-containing ascorbic acid derivative has ever been reported and the results below suggest why.

Attempts to generate either nitroso-ascorbic acid or nitro-ascorbic acid using this method (ascorbic acid plus less than stoichiometric concentrations of nitrite incubated in pH 3.7 in citrate buffer) resulted in complete loss of ascorbic acid (analyzed via HPLC), but no indication of a nitrosylated or nitrated product. The complete absence of any HPLC peaks with "aromatic" (closed furan-one ring structure in ascorbic acid) absorbance strongly suggested that ascorbic acid was oxidized to a ring-opened product (irreversibly oxidized). Moreover, complete loss of ascorbic acid in reactions containing a molar excess of ascorbic acid (over nitrite) means that ascorbic acid oxidation is catalytic, i.e., nitrosonium ion reacts with ascorbic acid to give some highly reactive product (or regenerates nitrite ion) that then reacts with a second ascorbic acid molecule, and so on, until all ascorbic acid is consumed. Even 1:10 ratios of nitrite to ascorbic acid ultimately oxidized all the ascorbic acid present.

Example 5

Analysis for the *Myriciaria dubia* Water Extract and Synthesized Compound

Figure 2A:
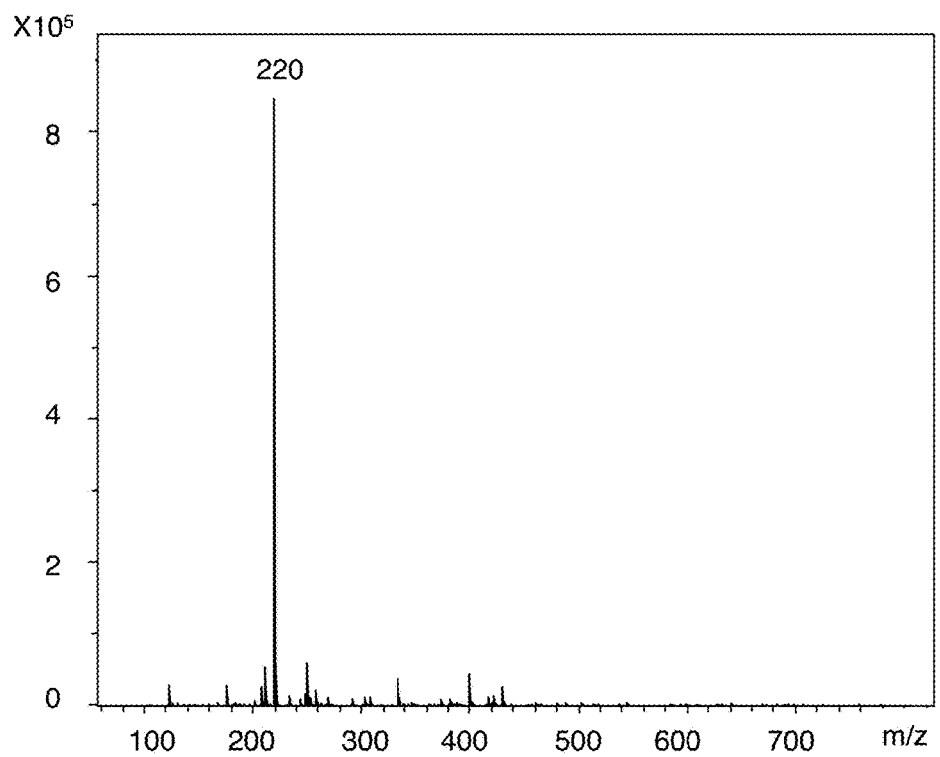
FIGS. 2A-2B show the results of mass spectrometry of compounds in Camu Camu fruit water extract.
Figure 2B:
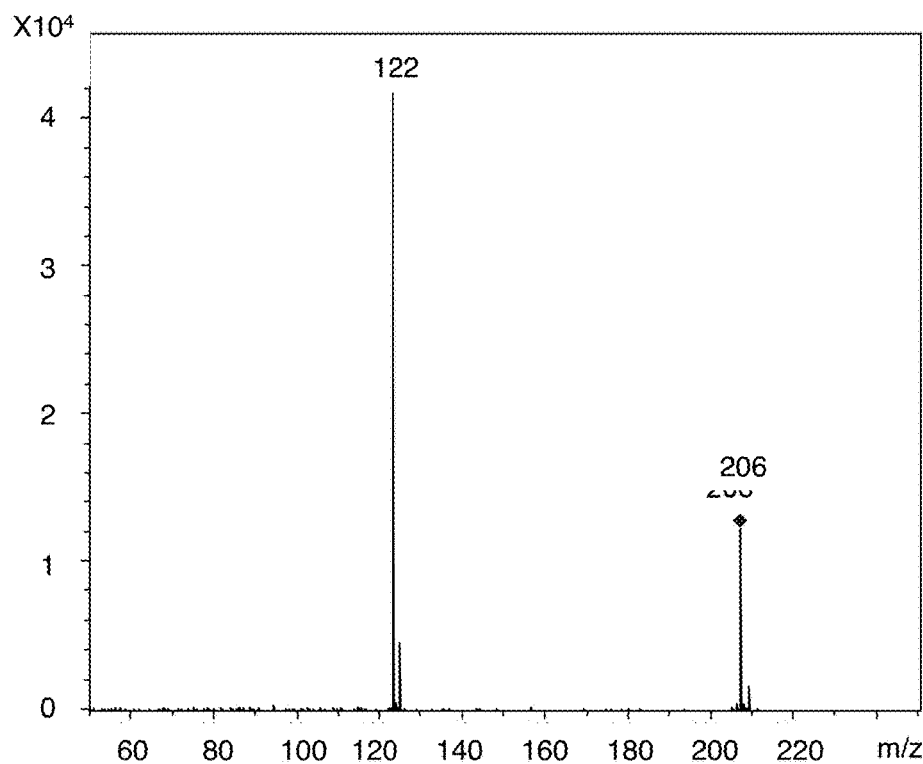
Figure 3A:
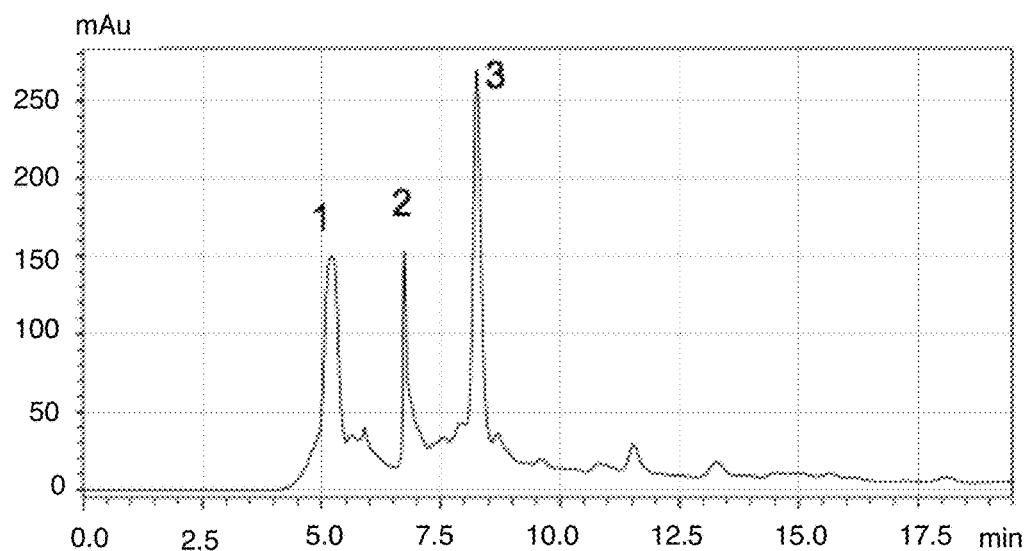
FIGS. 3A-3B show the results of chromatogram (HPLC) for camu camu fruit water extract and compound from synthetic reaction.
Figure 3B:
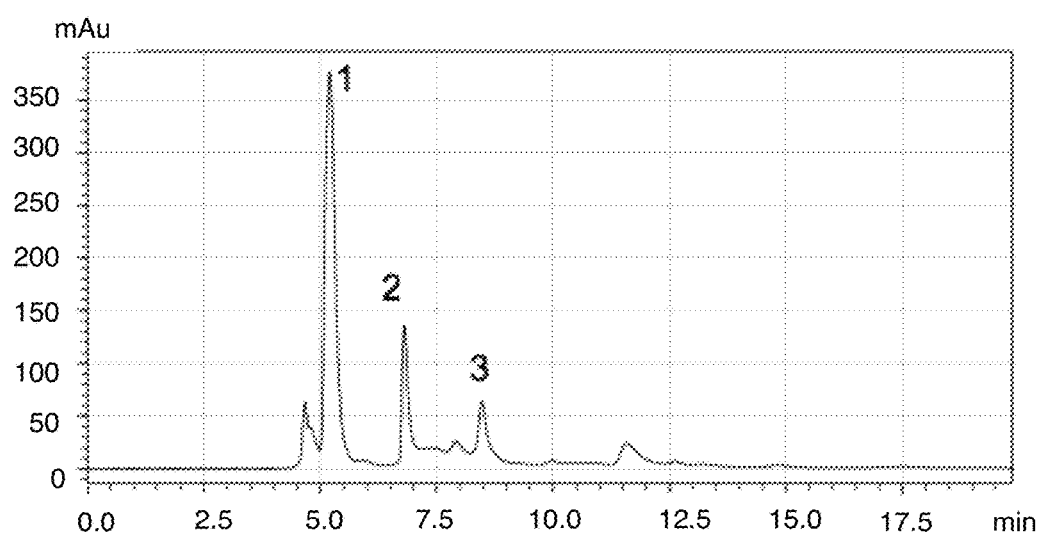
Figure 4A:
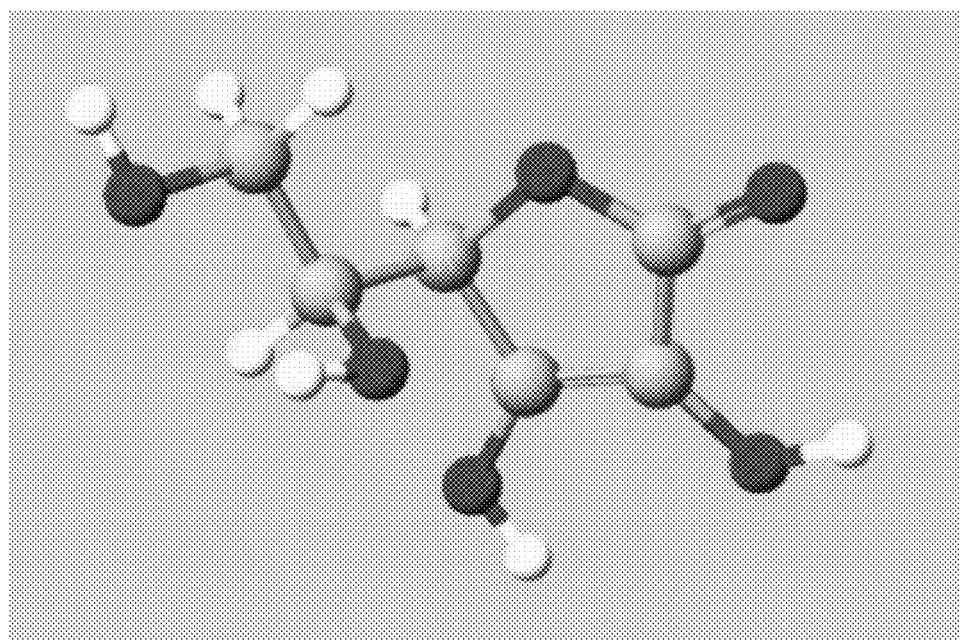
FIGS. 4A-4H show the geometry optimization, electron density, and UV-Visible spectra of authentic ascorbic acid and putative 3-nitroso-ascrobic acid.
Figure 4B:
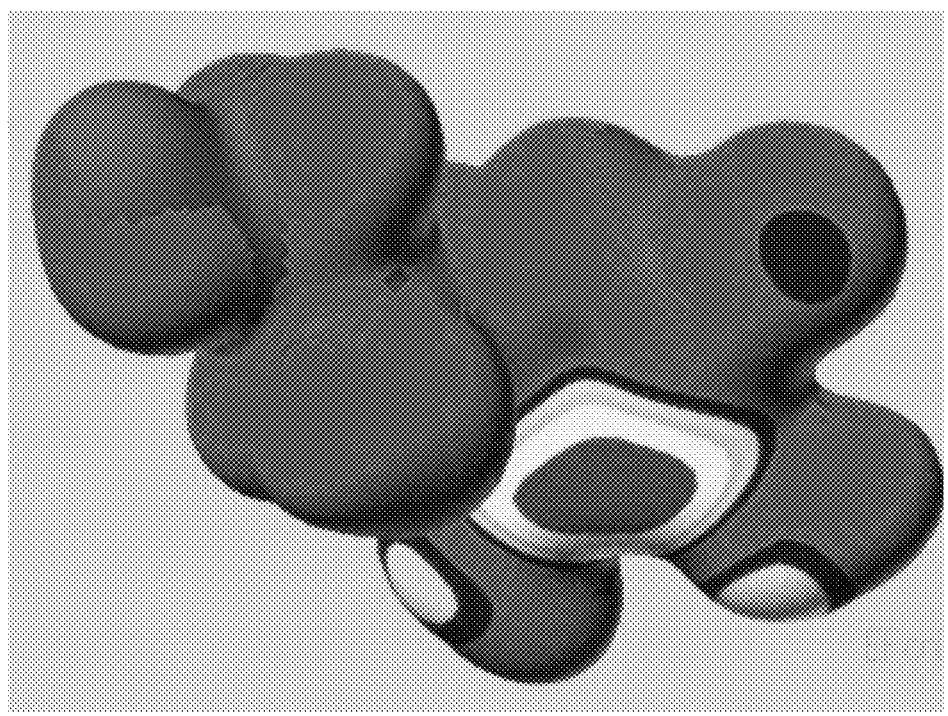
Figure 4C:
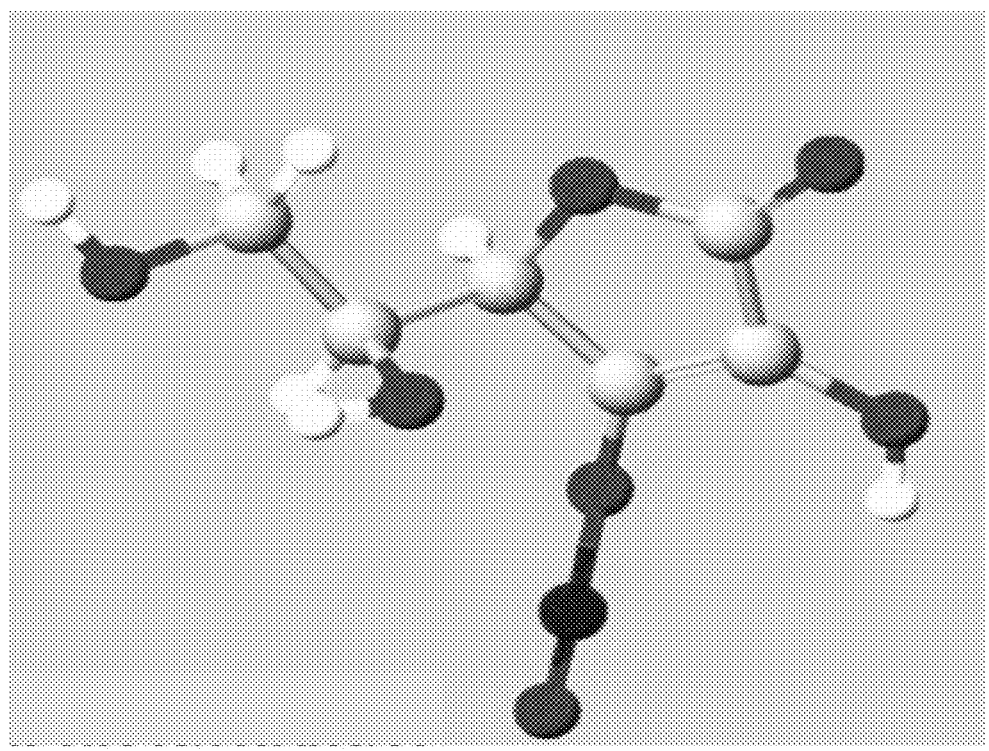
Figure 4D:
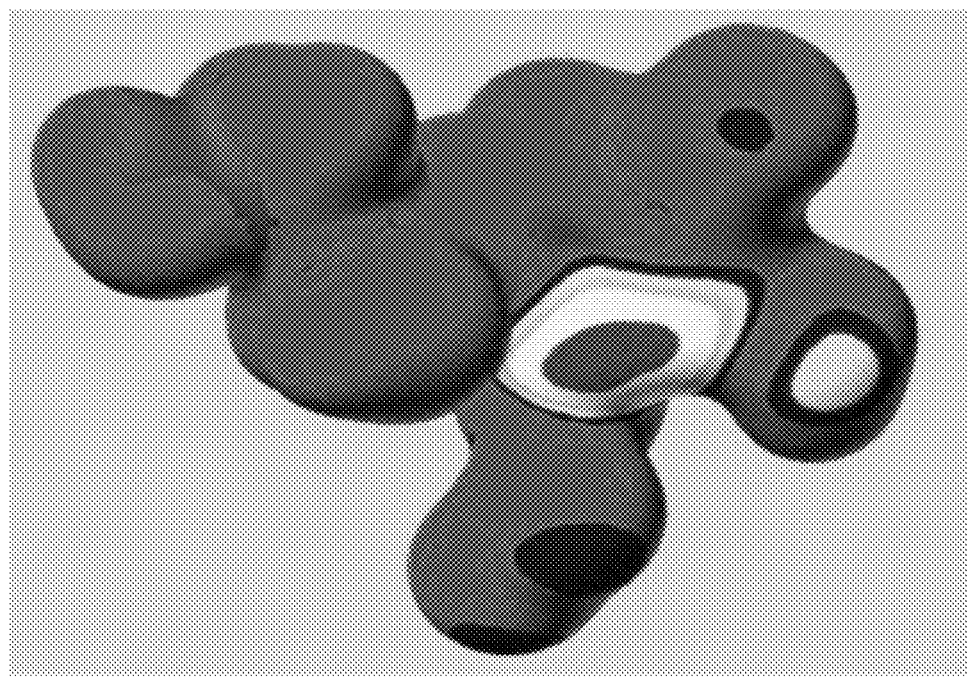
Figure 4E:
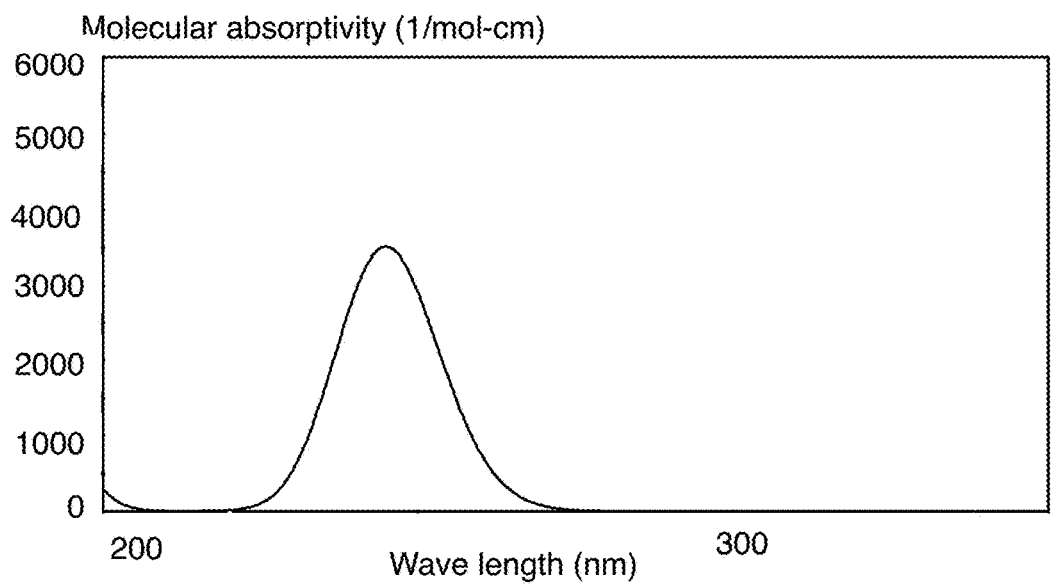
Figure 4F:
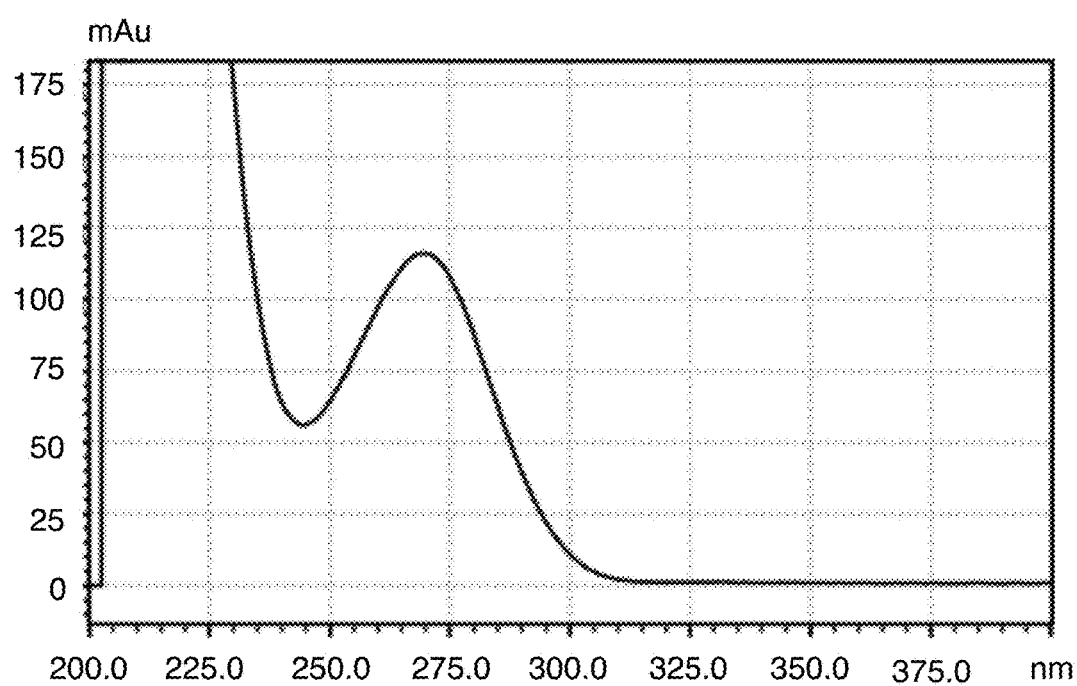
Figure 4G:
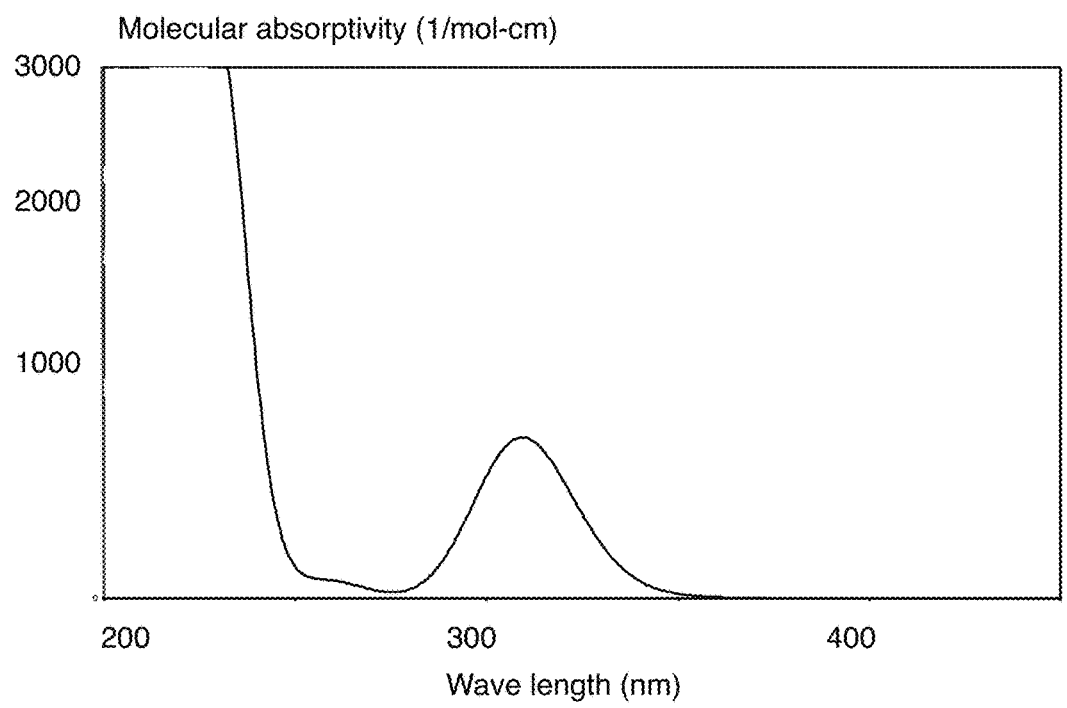
Figure 4H:
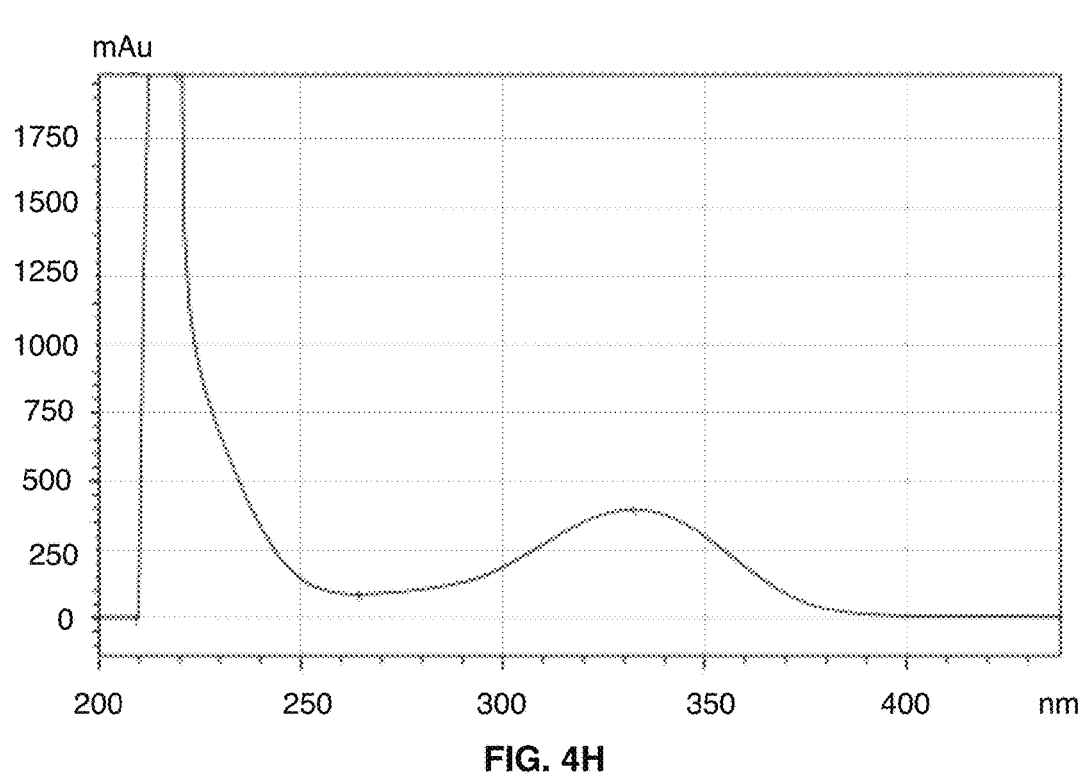

Preliminary mass spectrometry analysis has yielded masses (m/z) of parent peaks isolated from both camu and the synthetic reaction corresponding to both nitroso-ascorbic acid (m/z=206) and nitro-ascorbic acid (m/z=220) (FIGS. 2A-2B). Nitration of ascorbic acid is expected to displace one proton, yielding a m/z=221. However, because nitration could alter the pKa of other furan hydroxyl groups, an m/z=220 is not unexpected. Primary HPLC peaks (as monitored at 340 nm) from both camu and the synthetic reaction have the same retention times (FIGS. 3A-3B). The UV-visible spectra of compounds isolated both from camu water extracts and the synthetic reaction are virtually identical, and possess higher absorbances (320 to 400 nm range) associated with nitroso-nitro-containing compounds. (Ascorbic acid has no absorbance above ~305 nm.) The presence of higher absorbances is best explained on the basis of nitroso- or nitro-ascorbic acid species, suggesting nitroso-ascorbic acid and nitro-ascorbic acid because the possible products from the simple synthetic reaction (containing only ascorbic acid, nitrite, and hydrogen peroxide) are quite limited. That is, very few other products can be envisioned that contain both the higher absorbances and the intact furanone ring absorbance of ascorbic acid. The exact positions of nitroso- and/or nitro-groups on ascorbic acid cannot currently be assigned. However, positions 3, and 4, and 6 on the furan ring are electron-rich, and therefore the most likely sites of attack by electrophilic species.

The relative purity of collected fractions from both camu water extract and synthetic reaction are also assessed using analytical HPLC. Analytical columns are: 4.6×250 mm Waters Spherisorb ODS-II, 3 micron or 4.6×150 mm Waters Symmetry-Sheild, 3.5 micron. Samples are run using 50 mM formate buffer, pH 3.5, 50 mM acetate buffer, pH 4.8, or succinate buffer, pH 5.5. Relative purity and shift in retention is examined and compared. This analytical protocol is also used to estimate relative concentrations of all components of camu water extract and the synthetic reaction.

The results shows that two main products from the synthetic reaction match two dominant compounds in the camu water extract in terms of retention time on HPLC and UV-visible spectra (peaks #1 and 2, FIGS. 3A-3B); a third peak (from camu extract and the synthetic reaction) has a similar spectra and may be a geometric isomer thereof. The simplicity of the synthetic reaction greatly limits the possible products to nitroso- and nitro-containing compounds, and oxidized (ring-opened) products of ascorbic acid. This fact, in turn, helps in putative identification of the novel compounds from camu camu.

Example 6

Molecular Modeling

Figure 5A:
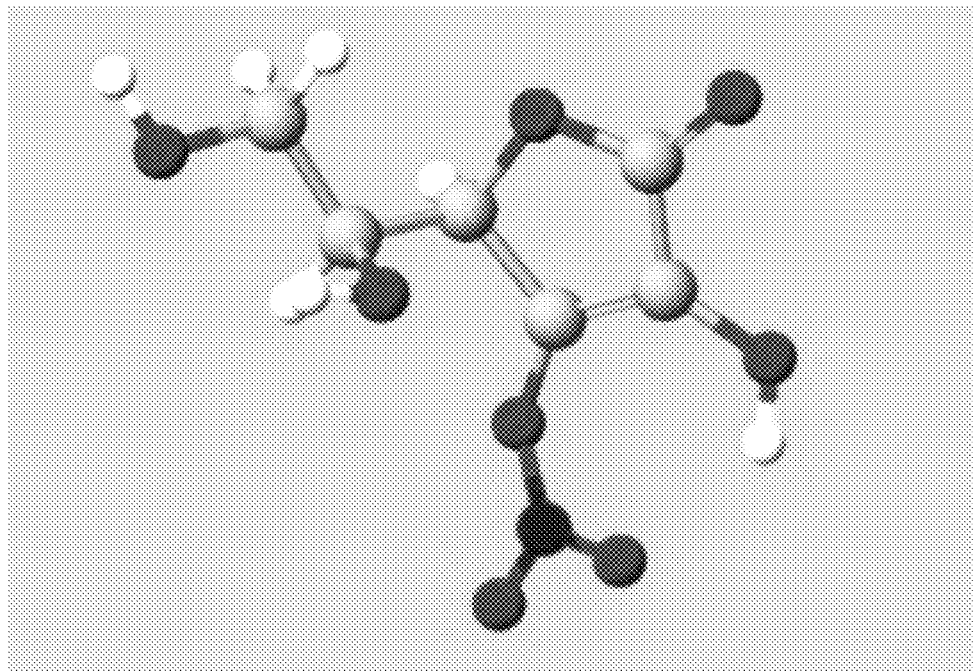
FIGS. 5A-5H show the geometry optimization, electron density, and UV-Visible spectra of putative 3-nitro-ascorbic acid and 4-nitroso-ascorbic acid.
Figure 5B:
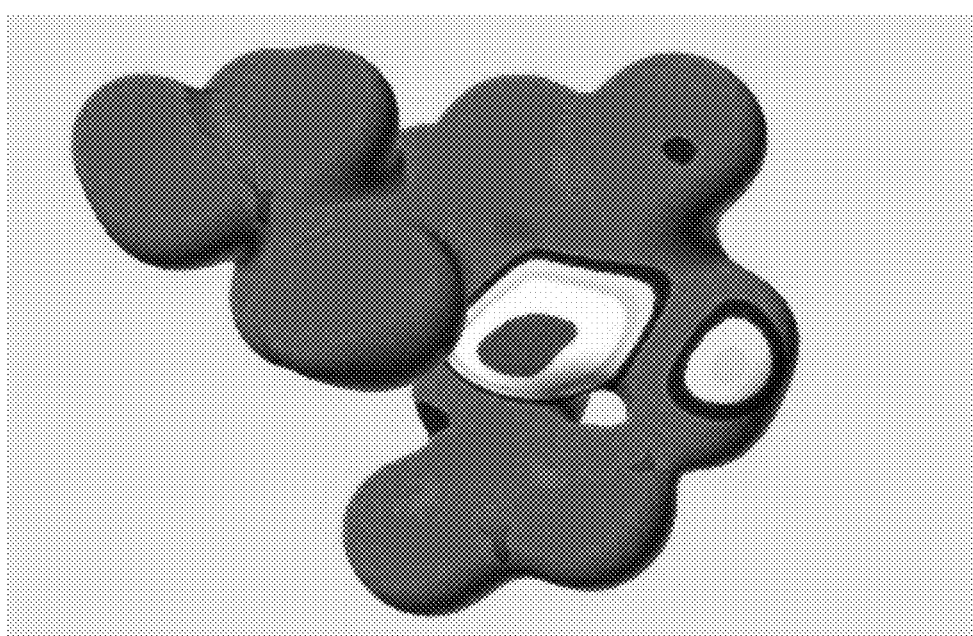
Figure 5C:
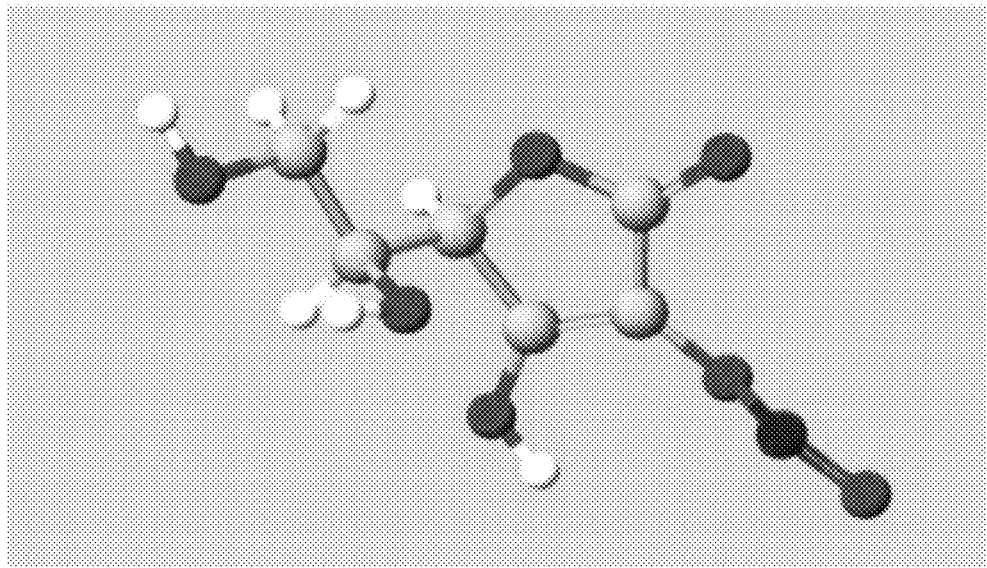
Figure 5D:
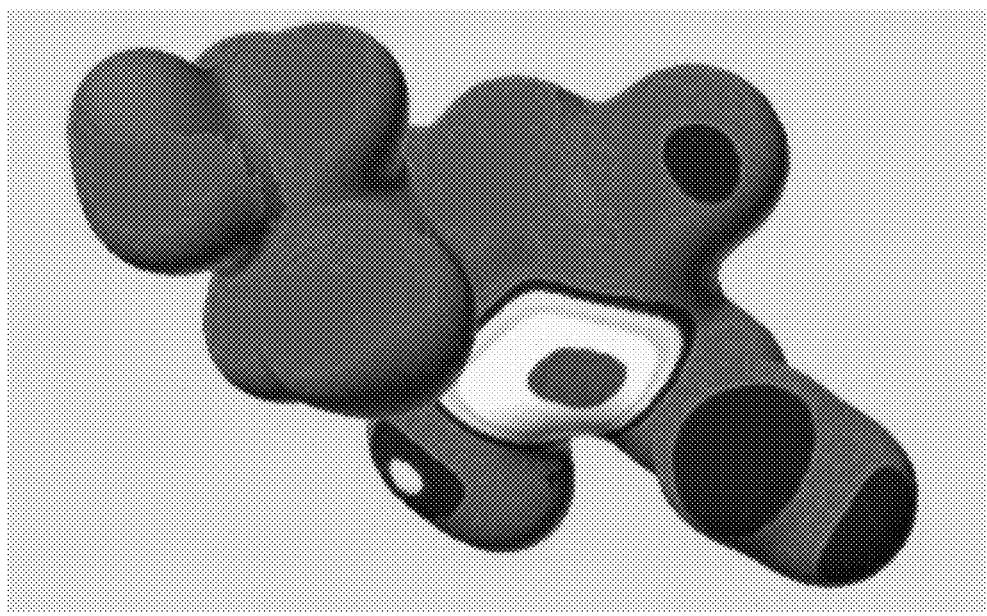
Figure 5E:
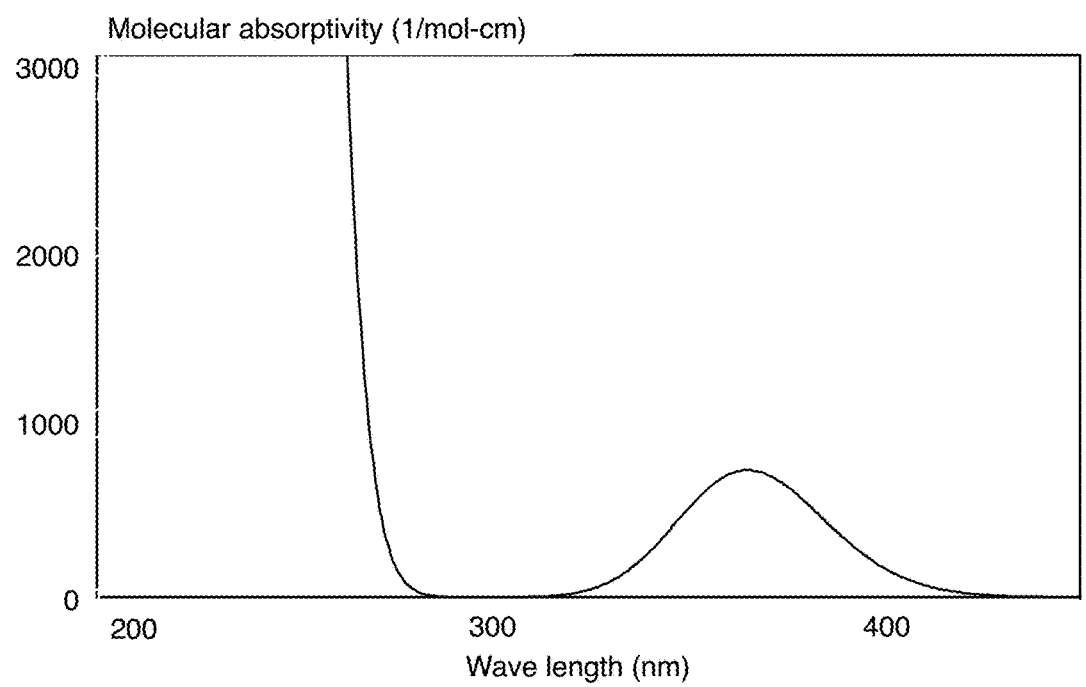
Figure 5F:
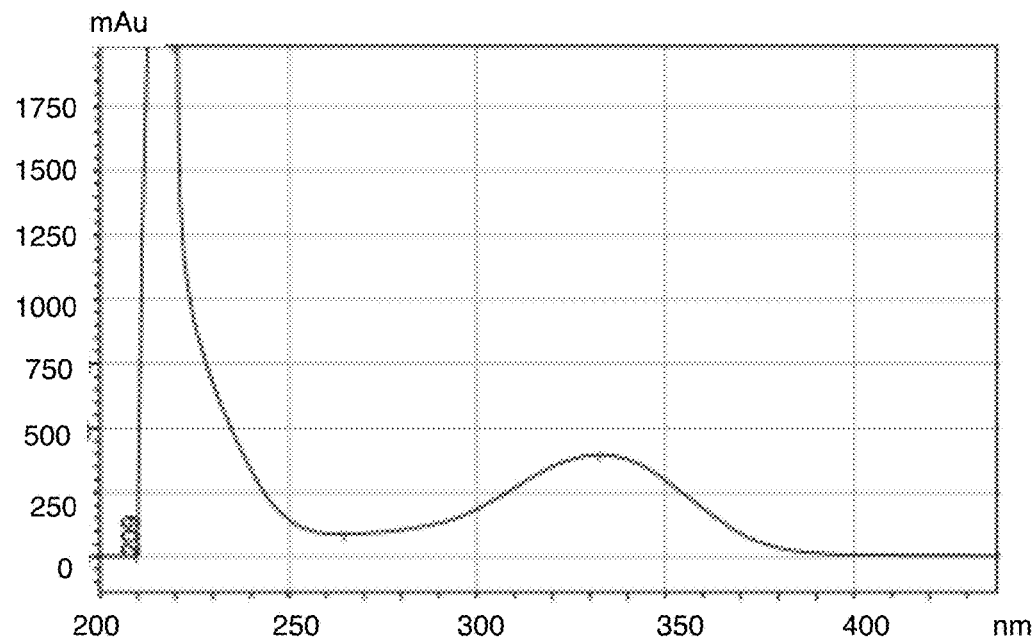
Figure 5G:
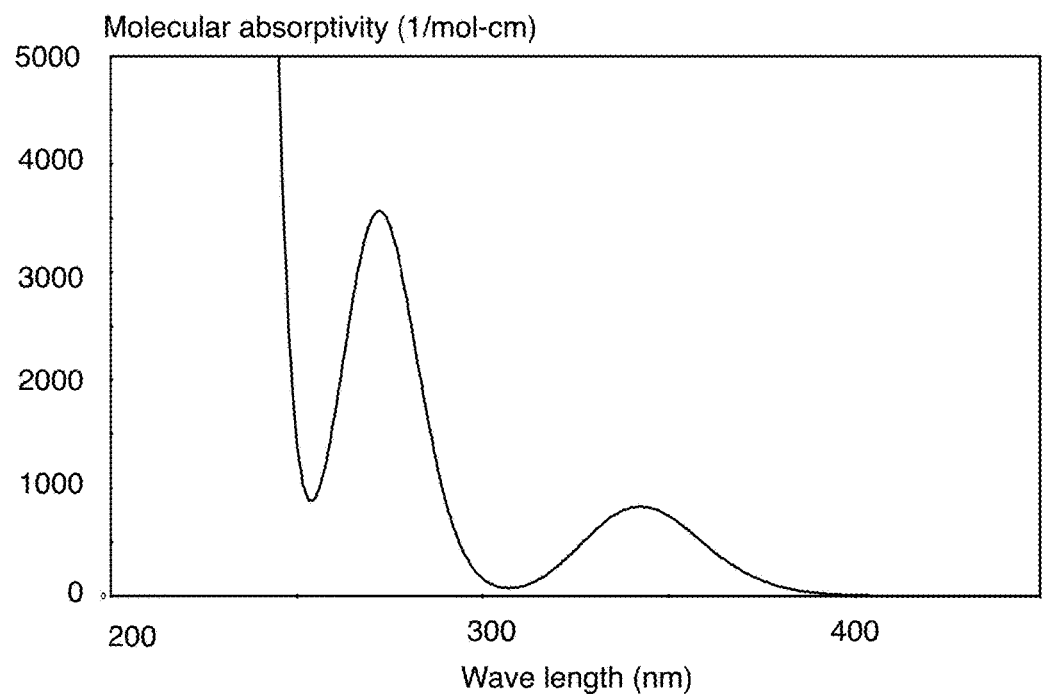
Figure 5H:
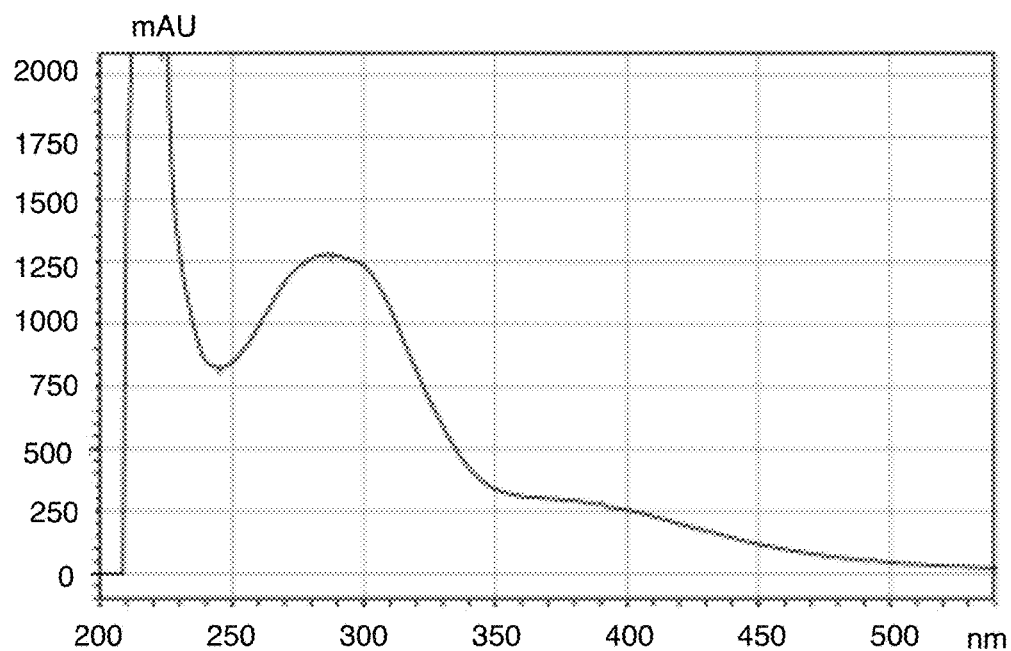

Molecular modeling of ascorbic acid, nitroso-, nitro-, and amino-containing analogs was compared to ascorbic acid. The results suggest that chemical (redox) properties that bestow biologically useful antioxidant activity to ascorbic acid, may also exist with these compounds and analogs. FIGS. 4A-4H and FIGS. 5A-5H show geometry optimization and calculated UV-visible spectra for ascorbic acid, 3-nitrosos-ascorbic acid, 3-nitro-ascorbic acid, and 4-nitroso-ascorbic acid. Spectra calculated using ab initio approaches and basis sets are compared with those measured from HPLC peaks 1, 2, and 3, and show good agreement. Calculated spectra for 4-nitro-, 6-nitroso-, and 6-nitro-analogs (not shown) were significantly different from observed spectra, thus those structural possibilities were eliminated. Both 3- and 4-nitroso-ascorbic acid would have the same mass (m/z=206), thus they could only be distinguished via different HPLC retention times and/or different UV-visible spectra. HPLC peak 3 from camu camu water extract has a spectrum very similar to calculated peaks for 4-nitroso-ascorbic acid (FIGS. 5F and 5H).

FIGS. 4B, 4D, 5B and 5D also show "reactive" electron densities for ascorbic acid, 3-nitrosos-ascorbic acid, 3-nitro-ascorbic acid, and 4-nitroso-ascorbic acid, as determined from the same ab initio calculations used for geometry optimization and UV-visible spectra. Specifically, the electron densities are based on susceptibility to attack by electrophilic species. They reveal that nitroso- and nitro-substitution of the furan ring of ascorbic acid do not fundamentally alter the electron-rich region of the molecule that makes it a good antioxidant (FIGS. 4B, 4D, 5B and 5D).

More specifically, molecular modeling of nitroso-, nitro-, and amino-analogs in 3, 4, and 6 positions of the furan ring (FIG. 4C) suggests that the electron rich regions of the furan ring, that give rise to antioxidant properties, remain. The reversible redox properties of ascorbic acid indicates that nitroso- and nitro-analogs have the potential to be novel nitric oxide donor compounds, although the precise conditions under which this might occur have yet to be determined.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention.

What is claimed is:

1. A method for synthesizing an $NO_{1-3}$ derivative of ascorbic acid, comprising:
   derivatizing an ascorbic acid via nitrosylation and/or nitration in a buffered ascorbic acid solution to produce the $NO_{1-3}$ ascorbic acid derivative.

2. The method of claim 1, wherein the derivatizing step comprises:
   adding independently hydrogen peroxide and sodium nitrite peroxide to a stirred solution of the ascorbic acid in a sodium citrate buffer to produce a peroxynitrite/peroxynitrous acid.

3. The method of claim 2, wherein the molar ratio of said hydrogen peroxide to sodium nitrite to ascorbic acid to sodium citrate is 1:0.8:2:8.

4. The method of claim 2, wherein said sodium citrate buffer maintains the pH value of said solution at about 3.7.

5. The method of claim 2, wherein said peroxynitrite/peroxynitrous acid is at steady state in the solution.

6. The method of claim 1, further comprising reducing at least one nitro group to an amine.

7. The method of claim 1, further comprising isolating and purifying the $NO_{1-3}$ ascorbic acid derivative.

8. The method of claim 1, wherein derivatizing said ascorbic acid occurs over a period of about 24 hours.

9. A method for synthesizing an ascorbic acid analog, comprising the steps of:
   adding hydrogen peroxide to a stirred buffered solution of ascorbic acid;
   adding sodium nitrite peroxide to said stirred buffered solution;
   stirring said solution continuously for about 24 hours;
   reducing zero or more nitro groups to an —NH$_2$ group;
   isolating said ascorbic acid analog from the stirred solution; and
   purifying said ascorbic acid analog.

10. The method of claim 9, wherein said stirred solution has a pH of about 3.7.

11. The method of claim 9, wherein said ascorbic acid analog has a chemical structure of:

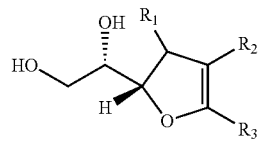

wherein R$_1$ is =O, —OH, —ONO, —ONO$_2$, or —NH$_2$; R$_2$ is —OH, —ONO, —ONO$_2$, or —NH$_2$; R$_3$ is —OH, =O, —ONO, —ONO$_2$ or NH$_2$, wherein at least one of R$_1$, R$_2$ and R$_3$ contains nitrogen.

12. The method of claim 11, wherein said ascorbic analog is 3-nitrosos-ascorbic acid, 3-nitro-ascorbic acid, or 4-nitroso-ascorbic acid.

* * * * *